United States Patent [19]

Lesher et al.

[11] 4,104,385
[45] Aug. 1, 1978

[54] CYCLIC ALKYLIDENYL N-[6-(AMINO)-3-PYRIDAZINYL]AMINOME-THYLENEMALONATES

[75] Inventors: George Y. Lesher; Chester J. Opalka, Jr., both of Schodack, N.Y.

[73] Assignee: Sterling Drug Inc., New York, N.Y.

[21] Appl. No.: 805,419

[22] Filed: Jun. 10, 1977

Related U.S. Application Data

[63] Continuation-in-part of Ser. No. 715,699, Aug. 19, 1976, abandoned.

[51] Int. Cl.² .......................................... C07D 405/12
[52] U.S. Cl. ..................................... 424/250; 542/420
[58] Field of Search ...................... 542/420; 424/250

[56] References Cited

U.S. PATENT DOCUMENTS 3,563,981  2/1971  Lesher .................................. 542/420

*Primary Examiner*—Arthur P. Demers
*Attorney, Agent, or Firm*—Robert K. Bair; B. Woodrow Wyatt

[57] ABSTRACT

Compounds useful as schistosomicidal agents are cyclic alkylidenyl N-[6-($R_3R_4N$)-4(or 5)-$R_5$-3-pyridazinyl]aminomethylenemalonates (I), where $R_3R_4N$ is lower-tertiary-amino and $R_5$ is hydrogen or lower-alkyl, are prepared by reacting 3-amino-6-($R_3R_4N$)-4(or 5)-$R_5$-pyridazine (III) with cyclic alkylidenyl α-(lower-alkoxymethylene)malonate (IV) or by heating equimolar quantities of III, tri-(lower-alkyl) orthoformate and cyclic alkylidenyl malonate (V). Also shown is cyclic isopropylidenyl N-(6-methylamino-3-pyridazinyl)aminomethylenemalonate, a schistosomicidal agent, and its preparation. Also shown are schistosomicidal compositions comprising as active component a schistosomicidally effective cyclic alkylidenyl N-[6-($R_3R_4N$)-4(or 5)-$R_5$-3-pyridazinyl]aminomethylenemalonate (I) or cyclic isopropylidenyl N-(6-methylamino-3-pyridazinyl)aminomethylenemalonate (II) or salt thereof and a method for the treatment of schistosomiasis which comprises administering to a host infected with schistosomes a schistosomicidally effective amount of said active component.

18 Claims, No Drawings

CYCLIC ALKYLIDENYL N-[6-(AMINO)-3-PYRIDAZINYL]AMINOMETHYLENEMALONATES

CROSS-REFERENCE TO RELATED APPLICATIONS

This application is a continuation-in-part of copending application Ser. No. 715,699, filed Aug. 19, 1976 and now abandoned.

BACKGROUND OF THE INVENTION (a) Field of the Invention

This invention relates to cyclic alkylidenyl N-(pyridazinyl)aminomethylenemalonate derivatives useful as schistosomicidal agents, to processes for their preparation and to compositions and a method for their use.

(b) Description of the Prior Art

The Sterling Drug Inc. Lesher U.S. Pat. No. 3,563,981, issued Feb. 16, 1971, discloses cyclic alkylidenyl N-Ar-aminomethylenemalonates to be useful as intermediates for preparing cyclized products, in turn, useful as intermediates for preparing antimalarials and anti-inflammatory agents. Also, said patent shows the cyclic alkylidenyl N-Ar-aminomethylenemalonates to have antiviral activity, e.g., against vaccinia virus in mice, and to be prepared by reacting an aromatic amine, Ar-NH$_2$, with a mixture of a trialkyl orthoformate and a cyclic alkylidenyl malonate. The patent defines "Ar" as "1-2 ringed aryl," that is, meaning "aromatic radicals having one or two aromatic rings which can be benzenoid or five- or six-membered heteroaromatic", including, inter alia, phenyl, naphthyl, pyridyl, quinolyl, pyridazinyl, etc. Preferred embodiments are the compounds where Ar is phenyl and substituted-phenyl, the latter having from one to three substituents illustrated, inter alia, by lower-alkyl, halo, nitro, amino, lower-alkylamino, lower-alkanoylamino, etc. This patent discloses at lines 30–35 of column 2 that the other said 1-2 ringed aryl radicals, e.g., inter alia, pyridazinyl, also can bear at available ring-carbon positions substituents such as those illustrated for the benzene ring of phenyl. The only specifically characterized compound where Ar is a pyridazinyl moiety is cyclic isopropylidenyl N-(6-methoxy-3-pyridazinyl)aminomethylenemalonate shown in the paragraph at lines 47–52 of column 29. Claim 18 defines isopropylidene 3-pyridazinylaminomethylenemalonate (same as cyclic isopropylidenyl N-(3-pyridazinyl)aminomethylenemalonate).

SUMMARY OF THE INVENTION

In one composition aspect, the invention relates to certain cyclic alkylidenyl N-[6-(R$_3$R$_4$N)-4(or 5)-R$_5$-3-pyridazinyl]aminomethylenemalonates (I) which are useful as schistosomicidal agents, preferred embodiments being I where R$_3$R$_4$N is dimethylamino, 4-morpholinyl or methylated-4-morpholinyl, R$_5$ is hydrogen and cyclic alkylidenyl is cyclic isopropylidenyl.

In another composition aspect, the invention relates to cyclic isopropylidenyl N-(6-methylamino-3-pyridazinyl)aminomethylenemalonate (II) which is useful as a schistosomicidal agent.

The invention in a process aspect comprises reacting 3-amino-6-(R$_3$R$_4$N)-4(or 5)-R$_5$-pyridazine (III) with cyclic alkylidenyl α-(lower-alkoxymethylene)malonate (IV) to produce I or, alternatively, comprises heating a mixture of equimolar quantities of III, tri-(lower-alkyl) orthoformate and cyclic alkylidenyl malonate (V) to produce I.

The invention in another process aspect comprises reacting 3-amino-6-methylaminopyridazine with isopropylidene α-(lower-alkoxy)methylenemalonate (IVa) or heating a mixture of equimolar quantities of 3-amino-6-methylaminopyridazine, tri-(lower-alkyl) orthoformate and cyclic isopropylidenyl malonate to produce II.

Another composition aspect of the invention resides in a schistosomicidal composition which comprises a pharmaceutically acceptable carrier and as the active component a schistosomicidally effective cyclic alkylidenyl N-[6-(R$_3$R$_4$N)-4(or 5)-R$_5$-3-pyridazinyl]aminomethylenemalonate (I) or cyclic isopropylidenyl N-(6-methylamino-3-pyridazinyl)aminomethylenemalonate (II), preferred active components being I where R$_1$ and R$_2$ are each methyl, R$_5$ is hydrogen and R$_3$R$_4$N is dimethylamino, 4-morpholinyl or methylated-4-morpholinyl.

The invention in a method aspect resides in the method for treating schistosomiasis which comprises administering orally to a host infected with schistosomes a schistosomacidally effective amount of I or II.

DETAILED DESCRIPTION INCLUSIVE OF PREFERRED EMBODIMENTS

The invention in a composition aspect resides in the class of compounds designated as cyclic alkylidenyl N-[6-(R$_3$R$_4$N)-4(or 5)-R$_5$-3-pyridazinyl]aminomethylenemalonate having the formula I

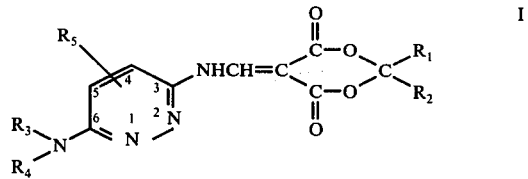

wherein

R$_1$ and R$_2$ are each lower-alkyl having from one to three carbon atoms;

R$_3$ and R$_4$ are each lower-alkyl having from one to three carbon atoms or R$_3$R$_4$N is 1-piperidinyl, 1-pyrrolidinyl, 4-methyl-1-piperazinyl, 4-morpholinyl or 4-morpholinyl having from one to four ring-carbon alkyl substituents selected from methyl, ethyl, n-propyl and isopropyl with the total number of carbon atoms of the alkyl substituent or substituents being from one to four;

R$_5$ is hydrogen or lower-alkyl having from one to three carbon atoms; or pharmaceutically acceptable salt thereof.

The compounds of formula I possess the inherent applied use characteristics of having schistosomicidal activity, as determined by proven chemotherapeutic evaluation procedures, and are useful as schistosomicidal agents. Preferred embodiments of this composition aspect of the invention are the compounds of formula I where R$_1$ and R$_2$ are each methyl, R$_5$ is hydrogen and R$_3$R$_4$N is dimethylamino, 4-morpholinyl or methylated-4-morpholinyl, that is, 4-morpholinyl having from one to four methyl substituents, a particularly preferred methylated-4-morpholinyl embodiment being 2,6-dimethyl-4-morpholinyl compound where R$_5$ is hydrogen and R$_1$ and R$_2$ are each methyl.

The invention in another composition aspect resides in the compound designated as cyclic isopropylidenyl N-(6-methylamino-3-pyridazinyl)aminomethylenemalonate having the formula II

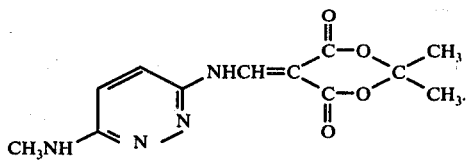

The compound of formula II possesses the inherent applied use characteristics of having schistosomicidal activity, as determined by proven chemotherapeutic evaluation procedures, and is useful as a schistosomicidal agent.

The invention in a process aspect comprises reacting 3-amino-4(or 5)-$R_5$-6-($R_3R_4N$)-pyridazine of the formula III

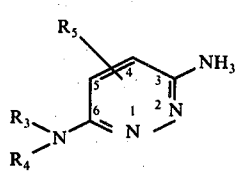

where $R_3$, $R_4$, $R_5$ and $R_3R_4N$ are defined as above for formula I, with a cyclic alkylidenyl α-(lower-alkoxymethylene)malonate of the formula IV

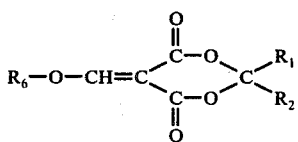

to produce the compound of formula I, where $R_6$ is loweralkyl, preferably methyl or ethyl, and $R_1$ and $R_2$ are each lower-alkyl as in formula I. Alternatively, this process aspect can be carried out by preparing IV in situ without its actual isolation by heating a mixture of equimolar quantities of the compound of formula III, tri-(lower-alkyl) orthoformate, preferably the triethyl ester, and cyclic alkylidenyl malonate of the formula V

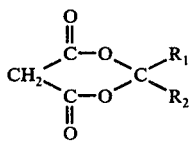

where $R_1$ and $R_2$ are each lower-alkyl as in I.

The invention in another process aspect comprises reacting 3-amino-6-methylaminopyridazine with isopropylidenyl α-(lower-alkoxy)methylenemalonate (IVa) to produce cyclic isopropylidenyl N-(6-methylamino-3-pyridazinyl)aminomethylenemalonate (II) or, alternatively, comprises heating a mixture of equimolar quantities of 3-amino-6-methylaminopyridazine, tri-(lower-alkyl) orthoformate, preferably the triethyl ester, and cyclic isopropylidenyl malonate (V where $R_1$ and $R_2$ are each methyl) to produce II.

Another composition aspect of the invention resides in a schistosomicidal composition which comprises as the active component a schistosomicidally effective cyclic alkylidenyl N-[6-($R_3R_4N$)-4(or 5)-$R_5$-3-pyridazinyl]aminomethylenemalonate having formula I or cyclic isopropylidenyl N-(6-methylamino-3-pyridazinyl)aminomethylenemalonate having formula II or pharmaceutically acceptable acid-addition salt thereof, where $R_1$, $R_2$, $R_3$, $R_4$, $R_5$ and $R_3R_4N$ are defined as in formula I in admixture with a pharmaceutically acceptable carrier. Preferred embodiments of this composition aspect of the invention are the schistosomicidal compositions having as the active component cyclic isopropylidenyl N-[6-($R_3R_4N$)-3-pyridazinyl]aminomethylenemalonate where $R_3R_4N$ is dimethylamino, 4-morpholinyl or methylated-4-morpholinyl.

A method aspect of the invention resides in the method for the treatment of schistosomiasis which comprises administering orally to a host infected with schistosomes a schistosomicidally effective amount of a compound selected from the group consisting of cyclic alkylidenyl N-[6-($R_3R_4N$)-4(or 5)-$R_5$-pyridazinyl]aminomethylenemalonate having formula I, cyclic isopropylidenyl N-(6-methylamino-3-pyridazinyl)aminomethylenemalonate having formula II or pharmaceutically acceptable acid-addition salt thereof. Particularly preferred embodiments of this aspect of the invention are said method using as the schistosomicidally effective compound cyclic isopropylidenyl N-[6-($R_3R_4N$)-3-pyridazinyl]aminomethylenemalonate where $R_3R_4N$ is dimethylamino, 4-morpholinyl or methylated-4-morpholinyl.

Also the compounds of formulas I and II are useful both in the free base form and in the form of acid-addition salts; and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal host organism in medicinal doses of the salts, so that the beneficial schistosomicidal properties inherent in the free base are not vitiated by side effects ascribable to the anions. In practicing the invention, it was found convenient to use the sulfate and hydrochloride salts, however, other appropriate pharmaceutically acceptable salts within the scope of the invention are those derived from mineral acids such as phosphoric acid and sulfamic acid; and organic acids such as acetic acid, citric acid, tartaric acid, lactic acid, methanesulfonic acid, ethanesulfonic acid, benzenesulfonic acid, p-toluenesulfonic acid, quinic acid, cyclohexylsulfamic acid, and the like giving the phosphate, sulfamate, acetate, citrate, tartrate, lactate, methanesulfonate, ethanesulfonate, benzenesulfonate, p-toluenesulfonate, quinate and cyclohexylsulfamate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

The molecular structures of the composition aspects I and II of the invention were assigned on the basis of evidence provided by infrared, ultraviolet, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of pharmaceutical chemistry to make and use the same, as follows:

The preparation of the compounds of formula I is carried out conveniently by stirring at room temperature (20°-25° C.) or by heating up to a temperature of about 80° to 120° C. the reactants, 3-amino-4(or 5)-$R_5$-6-($R_3R_4N$)-pyridazine (III) and cyclic alkylidenyl α-(lower-alkoxymethylene)malonate (IV), preferably in a molar ratio of 1:1 and preferably in the presence of a suitable inert solvent, e.g., a lower-alkanol, preferably methanol or ethanol. Other inert solvents can be used, e.g., acetonitrile, isopropyl alcohol, dimethylformamide, benzene, and the like. Alternatively, the above reaction can be carried out by preparing the reactant IV in situ without its actual isolation by heating a mixture of equimolar quantities of III, tri-(lower-alkyl) orthoformate, preferably the triethyl ester, and cyclic alkylidenyl malonate (V) using reaction conditions similar to those discussed above although here the reactants preferably were heated in a suitable inert solvent, preferably a lower-alkanol, e.g., ethanol, at about 60°-90° C.

The preparation of cyclic isopropylidenyl N-(6-methylamino-3-pyridazinyl)aminomethylenemalonate (II) is carried out as described above for the preparation of I but using a molar equivalent quantity of 3-amino-6-methylaminopyridazine in place of 3-amino-4(or 5)-$R_5$-6-($R_3R_4N$)-pyridazine (III) in the reaction with isopropylidenyl α-methoxymethylenemalonate or, alternatively, in the reaction with tri-(loweralkyl) orthoformate and cyclic isopropylidenyl malonate (V).

The intermediates used in the process aspects of the invention are either generally known or are prepared by generally known processes.

The intermediate 3-amino-4(or 5)-$R_5$-6-($R_3R_4N$)-pyridazines of formula III used to prepare the compounds of formula I are prepared by several generally known procedures which are described generally in the following paragraphs and are further illustrated hereinbelow in the specific exemplary disclosure.

In one procedure for preparing III, 6-chloropyridazine-3-carboxamide, a known compound [U.S. Pat. No. 3,042,673, issued July 3, 1962], is reacted with an amine of the formula $R_3R_4NH$, where $R_3$, $R_4$ and $R_3R_4N$ are defined as above for formulas I and III, to produce 6-($R_3R_4N$)-pyridazine-3-carboxamide, which is then converted to 3-amino-6-($R_3R_4N$)-pyridazine (III) by reaction with a reagent capable of converting carbamyl to amino, e.g., by reacting 6-($R_3R_4N$)-pyridazine-3-carboxamide in aqueous mixture with an alkali metal hypohalite, preferably sodium or potassium hypobromite or hypochlorite, and then acidifying the reaction mixture, preferably with an aqueous mineral acid, e.g., hydrochloric acid.

In another procedure for preparing III, 3-amino-6-chloropyridazine, a known compound [J. Druey et al., Helv. Chim. Acta 37, 121 (1954)], is autoclaved at about 140°-160° C. with an amine of the formula $R_3R_4NH$ to produce 3-amino-6-($R_3R_4N$)pyridazine (III).

In another procedure for preparing III, a generally known 6-($R_3R_4N$)-3-chloropyridazine [e.g., $R_5$ = H and $R_3R_4N$ = $(C_2H_5)_2N$, British Pat. No. 822,069, published Dec. 21, 1955; $R_5$ = H or 4-$CH_3$ or 5-$CH_3$ and $R_3R_4N$ = $(CH_3)_2N$, Acta Chemica Scandinavia 21, 2131 (1967); $R_3R_4N$ = piperidino, Helv. Chim. Acta 37, 121 (1954)], is reacted with sodium and liquid ammonia to produce III. This method has the disadvantage of producing a mixture containing III together with some starting 6-($R_3R_4N$)-3-chloropyridazine, although said mixture can be reacted with IV to produce the final product (I), which can be readily separated from the reaction mixture.

The intermediate amines of the formula $R_3R_4NH$ where $R_3R_4N$ is 4-morpholinyl having from one to four ring-carbon alkyl substituents selected from methyl, ethyl, n-propyl and isopropyl with the total number of carbon atoms of the alkyl substituent or substituents being from one to four are generally known and are prepared by conventional means. For example, 2-methylmorpholine, 3,3-dimethylmorpholine, 3-ethylmorpholine and 2-methyl-5-ethylmorpholine have been prepared by dehydration of the appropriate dialkanolamines, namely, N-β-hydroxyethyl-1-amino-2-propanol, N-β-hydroxyethyl-2-amino-2-methyl-1-propanol, N-β-hydroxyethyl-2-amino-1-butanol and N-β-hydroxy-n-propyl-2-amino-1-butanol, respectively [J. Org. Chem. 11, 286 (1946), which also shows a five-step preparation of 2-ethylmorpholine]. The same method was used to prepare 2-n-propylmorpholine, 2-isopropylmorpholine, 2,3-dimethylmorpholine and 5-ethyl-2,3-dimethylmorpholine using the appropriate dialkanolamines [Biochem. Pharmacol. 11, 639 (1962)]. Illustrative of other known alkylated-morpholines are the following: 3-methylmorpholine, 2,3-dimethylmorpholine, 2,5-dimethylmorpholine, 2,6-dimethylmorpholine, 3,5-dimethylmorpholine, 2,3,5-trimethylmorpholine, 2,3,3,-trimethylmorpholine, 2-ethyl-5-methylmorpholine, 5-ethyl-3-methylmorpholine, 2,6-diethylmorpholine, 2,2,6,6-tetramethylmorpholine and 3,3,5,5-tetramethylmorpholine.

The intermediate 3-amino-6-methylaminopyridazine used to prepare the compound of formula II is readily prepared by autoclaving the said known 3-amino-6-chloropyridazine with methylamine at about 150° C.

The following examples will further illustrate the invention without, however, limiting it thereto.

A. 6-($R_3R_4N$)PYRIDAZINE-3-CARBOXAMIDES

A-1. 6-(1-piperidinyl)pyridazine-3-carboxamide

A mixture containing 31.4 g. of 6-chloropyridazine-3-carboxamide, 34 g. of piperidine and 400 ml. of ethanol was refluxed for two hours and cooled. The precipitate was collected and washed successively with a small quantity of cold ethanol and ether, and dried. The resulting white solid was recrystallized from dimethylformamide, washed with ether and dried to yield 41 g. of 6-(1-piperidinyl)pyridazine-3-carboxamide, m.p. 251°-256° C.

It is contemplated that following the procedure described in Example A-1 but using in place of piperidine a molar equivalent quantity of the appropriate amine, $R_3R_4N$—H, the 6-($R_3R_4N$)-pyridazine-3-carboxamides of Examples A-2 thru A-12 will be obtained:

A-2. 6-(4-morpholinyl)pyridazine-3-carboxamide using morpholine.

A-3. 6-(1-pyrrolidinyl)pyridazine-3-carboxamide using pyrrolidine.

A-4. 6-Dimethylaminopyridazine-3-carboxamide using dimethylamine.

A-5. 6-(N-ethyl-N-methylamino)pyridazine-3-carboxamide using N-ethyl-N-methylamine.

A-6. 6-Diisopropylaminopyridazine-3-carboxamide using diisopropylamine.

A-7. 6-Di-n-propylaminopyridazine-3-carboxamide using di-n-propylamine.

A-8. 6-(4-methyl-1-piperazinyl)pyridazine-3-carboxamide using N-methylpiperazine.

A-9. 6-(2,6-dimethyl-4-morpholinyl)pyridazine-3-carboxamide using 2,6-dimethyl-4-morpholine.

A-10. 6-(2-methyl-4-morpholinyl)pyridazine-3-carboxamide using 2-methyl-4-morpholine.

A-11. 6-(3-methyl-4-morpholinyl)pyridazine-3-carboxamide using 3-methyl-4-morpholine.

A-12. 6-(2,5-dimethyl-4-morpholinyl)pyridazine-3-carboxamide using 2,5-dimethyl-4-morpholine.

B. 3-CHLORO-4(OR 5)-$R_5$-6-($R_3R_4N$)-PYRIDAZINES

B-1. 3-Chloro-5-(1-morpholinyl)pyridazine

A mixture containing 30 g. of 3,6-dichloropyridazine, 43.5 g. of morpholine and 400 ml. of ethanol was refluxed for four hours and allowed to cool. The solid that separated was collected, washed with ether and dried to yield, as a white solid, 23 g. of 3-chloro-6-(1-morpholinyl)pyridazine, m.p. 131°–134° C. Another 10 g. of this intermediate was obtained by stripping the mother liquor in vacuo, slurrying the residue with water, collecting the white solid, washing it with cold water and then drying it.

B-2. 3-Chloro-6-(1-pyrrolidinyl)pyridazine

A mixture containing 30 g. of 3,6-dichloropyridazine, 43 g. of pyrrolidine and 400 ml. of ethanol was refluxed for three hours and then allowed to stand at room temperature over the weekend. The solvent and excess pyrrolidine was distilled off in vacuo and the residue was slurried with water. The solid was collected, dried, recrystallized from 50% aqueous ethanol and dried to yield 36 g. of 3-chloro-6-(1-pyrrolidinyl)-pyridazine, m.p. 129°–131° C.

B-3. 3-Chloro-6-di-n-propylaminopyridazine

A mixture containing 30 g. of 3,6-dichloropyridazine, di-n-propylamine and 500 ml. of ethanol was refluxed for 24 hours, allowed to stand at room temperature overnight, and the solvent and excess di-n-propylamine distilled off in vacuo to yield, as a yellow semi-solid, 35 g. of 3-chloro-6-di-n-propylaminopyridazine, which was used directly in the next step, Example C-15. In another run using the same quantities of reactants, 600 ml. of ethanol and a reflux period of about fifteen hours and a standing period at room temperature over the weekend, followed by the purification procedure described in the next sentence, there was obtained 26 g. of off-white solid product, 3-chloro-6-di-n-propylaminopyridazine, m.p. 49°–51° C. The purification procedure was carried out by dissolving the reaction product in methylene dichloride, washing the methylene dichloride solution with water, drying the methylene dichloride solution over anhydrous sodium sulfate, distilling off the methylene dichloride in vacuo, recrystallizing the residue from n-hexane, washing the product with cold n-pentane and drying it in a vacuum oven at room temperature.

B-4. 3-Acetamido-6-chloro-5-methylpyridazine

A mixture containing 117 g. of 3,6-dichloro-4-methylpyridazine, 1.2 liters of ammonium hydroxide was heated in an autoclave at 120° C. for 6 hours. The reaction mixture was allowed to cool and the separated solid was collected, washed with water and dried. The mother liquor was heated in vacuo and the remaining solid was slurried up in cold water. The solid was collected, washed with cold water and dried. The two solid materials were combined and dried in a vacuum oven at 80° C. overnight (about fifteen hours). The combined dried solids (a mixture of 3-amino-6-chloro-5-methylpyridazine and 3-amino-6-chloro-4-methylpyridazine) were refluxed with 350 ml. of acetic anhydride for two hours and then allowed to stand at room temperature for about fifteen hours. The separated solid was collected by filtration and washed with ether and dried to yield, as an off-white solid, 24 g. of one isomer, namely, 3-acetamido-6-chloro-5-methylpyridazine, m.p. 214°–217° C. The mother liquor from the original filtration was concentrated and treated with about 200 ml. of ether. The resulting solid was collected, washed with ether and dried, followed by recrystallization from ethyl acetate, washing with ether and dried to yield another 14 g. of 3-acetamido-6-chloro-5-methylpyridazine, m.p. 212°–216° C.

C. 3-AMINO-4(OR 5)-$R_5$-6-($R_3R_4N$)PYRIDAZINES

C-1. 3-Amino-6-dimethylaminopyridazine

A mixture containing 29 g. of 3-amino-6-chloropyridazine, 100 g. of anhydrous dimethylamine and 450 ml. of absolute ethanol was autoclaved at 150° C. for fourteen hours (250 p.s.i.) and then allowed to cool and stand at room temperature over the weekend. The reaction mixture was distilled in vacuo to remove the solvent and excess dimethylamine to yield a yellow solid residue. The residue was recrystallized from 250 ml. of absolute ethanol, washed successively with cold ethanol and ether, and dried to yield, as a yellow solid, 24 g. of 3-amino-6-dimethylaminopyridazine hydrochloride, m.p. 187°–190° C.

In another run a mixture of 453 g. of 3-amino-6-chloropyridazine, 800 g. of anhydrous dimethylamine and 4.0 liters of absolute ethanol was autoclaved at 150° C. for fourteen hours. The reaction mixture was concentrated to a volume of about 1 liter, chilled and the pale orange solid was collected. A second crop was obtained by concentrating the ethanolic solution to a volume of about 400 and chilling. Both crops were dried over the weekend in vacuo at 65° C. The yield of the first crop was 280 g. of 3-amino-6-dimethylaminopyridazine hydrochloride, m.p. 193°–195° C. The second crop weighed 163 g. and melted at 193°–211° C. The second crop was recrystallized from ethanol and dried overnight at 65° C. to give 115 g. of 3-amino-6-dimethylaminopyridazine hydrochloride, m.p. 193°–198° C.

In another run preparing 3-amino-6-dimethylaminopyridazine, a mixture containing 312 g. of 3-amino-6-chloropyridazine, 275 g. (405 ml.) of anhydrous dimethylamine and 1200 ml. of absolute ethanol was autoclaved at 150° C. for 15 hours. The reaction mixture was concentrated in vacuo to a volume of about 700 ml. and chilled. The solid was collected, washed successively with cold ethanol and ether, and then air dried to give 150 g. of 3-amino-6-dimethylaminopyridazine hydrochloride, m.p. 193°–215° C. The filtrate was concentrated to a volume of 400 ml. and chilled. The resulting precipitate was collected, washed as above and air dried to yield 100 g. of said product, m.p. 190°–220° C. The 150 g. of the first crop was dissolved in 600 ml. of ethanol on a steam bath, adding aqueous sodium hydroxide solution slowly to achieve solution and a resulting pH of about 9. The separated sodium chloride was filtered off from the solution after cooling it to room temperature and the sodium chloride was washed with isopropyl alcohol. The combined filtrate and isopropyl alcohol washings were concentrated to remove practically all of the ethanol while at the same time adding isopropyl alcohol, the final volume being about 250 ml. The solution was cooled and the crystalline precipitate was collected, washed successively with cold isopropyl alcohol and ether to yield, as yellow crystals, 76 g. of 3-amino-6-dimethylaminopyridazine in free base form, m.p. 133°–135° C. A small sample of this free base form was converted into its dihydrochloride, m.p. 273°–275° C.

C-2. 3-Amino-6-diethylaminopyridazine

A small piece of sodium from a 11.5 g. portion thereof was added to 750 ml. of liquid ammonia with stirring. To the stirred mixture was added 100 mg. of ferric nitrate followed by the rest of the 11.5 g. of sodium in portions. The resulting mixture was stirred for 2½ hours and to the stirred mixture was added dropwise a solution containing 38 g. of 3-chloro-6-diethylaminopyridazine and 100 ml. of tetrahydrofuran. The resulting reaction mixture was stirred at room temperature for about 24 hours and water was added with stirring to decompose the excess sodamide. The mixture was stirred until all of the ammonia evaporated and the solvent and then distilled off in vacuo. To the residue was added water and the aqueous mixture was extracted with methylene dichloride. The organic extract was dried over anhydrous sodium sulfate, treated with decolorizing charcoal and filtered. The filtrate was evaporated in vacuo to yield 29 g. of a dark oil containing (about 50%) 3-amino-6-diethylaminopyridazine which was used in the subsequent preparation (see Example D-2) without any further purification.

C-3. 3-Amino-6-(4-morpholinyl)pyridazine

Following the procedure described in Example C-2 using 750 ml. of liquid ammonia, 11.5 g. of sodium, 33 g. of 3-chloro-6-(4-morpholinyl)pyridazine and 225 ml. of tetrahydrofuran, there was obtained 11 g. of dark glassy material containing (about 30%) 3-amino-6-(4-morpholinyl)pyridazine which was used in Example D-3 without purification.

C-4. 3-Amino-6-(1-pyrrolidinyl)pyridazine

Following the procedure described in Example C-2 using 5 g. of sodium, 500 ml. of liquid ammonia, 18 g. of 3-chloro-6-(1-pyrrolidinyl)-pyridazine and 125 ml. of tetrahydrofuran, there was obtained 16 g. of crystalline material which, as indicated by TLC analysis, is a 50/50 mixture of the 3-chloro starting material and 3-amino product. A small sample of the crystalline material was recrystallized from ethyl acetate and sent in for mass spectrographic analysis which indicated a mixture of said starting material and product. The crystalline mixture obtained in this preparation was estimated to contain about 8 g. of 3-amino-6-(1-pyrrolidinyl)pyridazine and was used in the subsequent reaction (see Example D-4, first paragraph) as a mixture without any further purification.

A better procedure for preparing 3-amino-6-amino-6-(1-pyrrolidinyl)pyridazine is given as follows: a mixture containing 80 g. of 3-amino-6-chloropyridazine, 105 ml. of pyrrolidine, 1.2 liters of N,N-dimethylaniline and 1 g. of copper bronze powder was heated with stirring at 130°–135° C. for 18 hours. When a TLC test indicated that starting material was still present, an additional 50 ml. portion of pyrrolidine in 200 ml. of N,N-dimethylaniline was added to the reaction mixture followed by more copper bronze powder and the reaction mixture was heated for an additional 24 hours. The reaction mixture was cooled to 30° C. and filtered. The filtrate was concentrated under oil pump vacuum to leave a crystalline solid. The solid was slurried with isopropyl alcohol while chilling the mixture in an ice bath. The solid was collected, washed with a small amount of cold isopropyl alcohol and dried in a vacuum oven at 60° C. to produce 53 g. (76% yield) of 3-amino-6-(1-pyrrolidinyl)-pyridazine, m.p. 209°–211° C. A TLC check of the filtrate indicated that it contained more of the product, which was not isolated. The intermediate 3-amino-6-(1-pyrrolidinyl)pyridazine prepared by said better procedure was used in the preparation of the final product as described in the second paragraph of (Example D-4) described hereinbelow.

C-5. 3-Amino-6-(1-piperidinyl)pyridazine

To a solution containing 78.4 g. of potassium hydroxide in 400 ml. of water at 0° C. was added dropwise 24 g. (8.2 ml.) of bromine with stirring. To the stirred reaction mixture at 0° C. was added 41 g. of 6-(1-piperidinyl)pyridazine-3-carboxamide and the resulting reaction mixture was stirred at 0° C. for 15 minutes and then stirred overnight at room temperature. The reaction mixture was then heated on a steam bath for about fifteen minutes and was cooled. To the reaction mixture was added 6N hydrochloric acid until acidic and then the mixture was basified with 2N aqueous potassium hydroxide solution and cooled. The precipitated product was collected, washed with water, dried, recrystallized from dimethylformamide, washed successively with ethanol and ether and dried to yield as a yellow solid 20 g. of 3-amino-6-(1-piperidinyl)pyridazine, m.p. 245°–153° C.

It is contemplated that following the procedure described in Example C-5 but using in place of 6-(1-piperidinyl)-pyridazine-3-carboxamide a molar equivalent quantity of the appropriate 6-($R_3R_4N$)-pyridazine-3-carboxamide, the 3-amino-6-($R_3R_4N$)-pyridazines of Examples C-6 thru C-12 will be obtained:

C-6. 3-Amino-6-(4-morpholinyl)pyridazine using 6-(4-morpholinyl)pyridazine-3-carboxamide.

C-7. 3-Amino-6-(1-pyrrolidinyl)pyridazine using 6-(1-pyrrolidinyl)pyridazine-3-carboxamide.

C-8. 3-Amino-6-dimethylaminopyridazine using 6-dimethylaminopyridazine-3-carboxamide.

C-9. 3-Amino-6-(N-ethyl-N-methylamino)pyridazine using 6-(N-ethyl-N-methylamino)pyridazine-3-carboxamide.

C-10. 3-Amino-6-diisopropylaminopyridazine using 6-diisopropylaminopyridazine-3-carboxamide.

C-11. 3-Amino-6-di-n-propylaminopyridazine using 6-di-n-propylaminopyridazine-3-carboxamide.

C-12. 3-Amino-6-(4-methyl-1-piperazinyl)pyridazine using 6-(4-methyl-1-piperazinyl)-3-carboxamide.

C-13. 3-Amino-6-(1-piperidinyl)pyridazine

A mixture containing 13.0 g. of 3-amino-6-chloropyridazine and 50 ml. of piperidine was refluxed with stirring for 1 week. A TLC spot plate test (75% ethyl acetate and 25% methanol) indicated that the mixture was mostly product but a small amount of starting material was still present. The reaction mixture was evaporated to dryness and the resulting tan solid was triturated with 150 ml. of water. Some beige-colored solid (starting material) was filtered off, washed with a little fresh water and dried in a vacuum oven at 80° C. to give 3.2 g. of 3-amino-6-chloropyridazine (25% recovery). The combined aqueous filtrates were evaporated to dryness to produce 20.2 g. of yellow solid consisting mostly (up to 17.8 g.) 3-amino-6-(1-piperidinyl)-pyridazine and some piperidine hydrochloride, which was used directly in Example D-5 without further purification.

C-14. 3-Amino-6-(4-methyl-1-piperazinyl)pyridazine

A mixture containing 50 ml. of N-methylpiperazine and 13 g. of 3-amino-6-chloropyridazine was refluxed with stirring for eighteen hours and then distilled to dryness on a rotary evaporator to yield 39.4 g. of a viscous liquid residue. The residue was dissolved in 100 ml. of water and filtered. The filtrate was distilled to dryness on a rotary evaporator to produce 33.7 g. of a viscous red syrup which is a mixture of 3-amino-6-(4-methyl-1-piperazinyl)pyridazine and a molar equivalent quantity of N-methylpiperazine hydrochloride. This material was used in Examples D-9 without further treatment.

C-15. 3-Amino-6-di-n-propylaminopyridazine

Following the procedure described in Example C-2 using 900 ml. of liquid ammonia, 13.8 g. of sodium, 35 g. of 3-chloro-6-di-n-propylaminopyridazine and 100 ml. of tetrahydrofuran, there was obtained, as a black oily material, 13 g. of 3-amino-6-di-n-propylaminopyridazine which was used in Example D-8 without purification.

C-16. 3-Amino-6-(2,6-dimethyl-4-morpholinyl)pyridazine

A mixture containing 12.9 g. of 3-amino-6-chloropyridazine and 46 g. of 2,6-dimethylmorpholine was refluxed for six hours and then allowed to stand at room temperature overnight (about 15 hours). A TLC spot plate check using 3:1 of ethyl acetate:methanol indicated no remaining starting material. The reaction mixture was heated in vacuo to remove the excess 2,6-dimethylmorpholine and the remaining material was acidified with 6N hydrochloric acid with cooling. The solid that separated was collected and dried in vacuo at 80° C. The solid was recrystallized from ethanol, washed with ether and dried in vacuo at 80° C. to yield 9 g. of 3-amino-6-(2,6-dimethyl-4-morpholinyl)pyridazine hydrochloride, m.p. 222°–225° C.

In a second run a mixture of 52.4 g. of 3-amino-6-chloropyridazine and 200 ml. (185 g.) of 2,6-dimethylmorpholine was refluxed for five hours and then heated in vacuo to remove the excess 2,6-dimethylmorpholine. The remaining dark reddish gummy material was dissolved in 400 ml. of warm water and made alkaline with 34 ml. of 10% aqueous sodium hydroxide solution. The water was distilled off in vacuo and to the residue was added 500 ml. of isopropyl alcohol. The isopropyl alcohol was then distilled off in vacuo and the residue was recrystallized from 400 ml. of isopropyl acetate and the product dried in vacuo at 70° C. to produce 48 g. of 3-amino-6-(2,6-dimethyl-4-morpholinyl)pyridazine, m.p. 128°–130° C. A second crop of 11 g. of this compound, m.p. 127°–129° C. was obtained from the mother liquor.

C-17. 3-Amino-6-dimethylamino-5-methylpyridazine

A mixture containing 24 g. of 3-acetamido-6-chloro-5-methylpyridazine and 125 ml. of 40% aqueous dimethylamine was heated in an autoclave at 120° C for 24 hours. The separated solid of the reaction mixture was collected, washed with water, dried, recrystallized from 50% aqueous ethanol and dried in vacuo at 80° C. to produce 11 g. of 3-amino-6-dimethylamino-5-methylpyridazine, m.p. 194°–199° C.

It is contemplated that following the procedure described in Example C-16 but using in place of 2,6-dimethylmorpholine a molar equivalent quantity of the appropriate C-alkylated-morpholine, there will be obtained the following respective 3-amino-6-(C-alkylated-4-morpholinyl)pyridazines of Examples C-18 thru C-37.

C-18. 3-Amino-6-(2-methyl-4-morpholinyl)pyridazine using 2-methylmorpholine.

C-19. 3-Amino-6-(3-methyl-4-morpholinyl)pyridazine using 3-methylmorpholine.

C-20. 3-Amino-6-(2-ethyl-4-morpholinyl)pyridazine using 2-ethylmorpholine.

C-21. 3-Amino-6-(3-ethyl-4-morpholinyl)pyridazine using 3-ethylmorpholine.

C-22. 3-Amino-6-(2-n-propyl-4-morpholinyl)pyridazine using 2-n-propylmorpholine.

C-23. 3-Amino-6-(2-isopropyl-4-morpholinyl)pyridazine using 2-isopropylmorpholine.

C-24. 3-Amino-6-(3-n-propyl-4-morpholinyl)pyridazine using 3-n-propylmorpholine.

C-25. 3-Amino-6-(2,3-dimethyl-4-morpholinyl)-pyridazine using 2,3-dimethylmorpholine.

C-26. 3-Amino-6-(2,5-dimethyl-4-morpholinyl)-pyridazine using 2,5-dimethylmorpholine.

C-27. 3-Amino-6-(3,5-dimethyl-4-morpholinyl)-pyridazine using 3,5-dimethylmorpholine.

C-28. 3-Amino-6-(3,3-dimethyl-4-morpholinyl)-pyridazinyl using 3,3-dimethylmorpholine.

C-29. 3-Amino-6-(2-ethyl-5-methyl-4-morpholinyl)-pyridazinyl using 2-ethyl-5-methylmorpholine.

C-30. 3-Amino-6-(5-ethyl-3-methyl-4-morpholinyl)-pyridazinyl using 5-ethyl-3-methylmorpholine.

C-31. 3-Amino-6-(5-ethyl-2-methyl-4-morpholinyl)-pyridazinyl using 5-ethyl-2-methylmorpholine.

C-32. 3-Amino-6-(2,6-diethyl-4-morpholinyl)-pyridazinyl using 2,6-diethylmorpholine.

C-33. 3-Amino-6-(2,3,5-trimethyl-4-morpholinyl)-pyridazinyl using 2,3,5-trimethylmorpholine.

C-34. 3-Amino-6-(2,3,3-trimethyl-4-morpholinyl)-pyridazinyl using 2,3,3-trimethylmorpholine.

C-35. 3-Amino-6-(5-ethyl-2,3-dimethyl-4-morpholinyl)pyridazinyl using 5-ethyl-2,3-dimethylmorpholine.

C-36. 3-Amino-6-(2,2,6,6-tetramethyl-4-morpholinyl)pyridazinyl using 2,2,6,6-tetramethylmorpholine.

C-37. 3-Amino-6-(3,3,5,5-tetramethyl-4-morpholinyl)pyridazinyl using 3,3,5,5-tetramethylmorpholine.

It is contemplated that following the procedure described in Example C-5 but using in place of 6-(1-piperidinyl)pyridazine-3-carboxamide a molar equivalent quantity of the appropriate 6-($R_3R_4N$)-pyridazine-3-carboxamide, the 3-amino-6-($R_3R_4N$)-pyridazines of Examples C-38 thru C-41 will be obtained:

C-38. 3-Amino-6-(2,6-dimethyl-4-morpholinyl)-pyridazine using 6-(2,6-dimethyl-4-morpholinyl)pyridazine-3-carboxamide.

C-39. 3-Amino-6-(2-methyl-4-morpholinyl)pyridazine using 6-(2-methyl-4-morpholinyl)pyridazine-3-carboxamide.

C-40. 3-Amino-6-(3-methyl-4-morpholinyl)pyridazine using 6-(3-methyl-4-morpholinyl)pyridazine-3-carboxamide.

C-41. 3-Amino-6-(2,5-dimethyl-4-morpholinyl)-pyridazine using 6-(2,5-dimethyl-4-morpholinyl)pyridazine-3-carboxamide.

C-42. 3-Amino-6-(4-morpholinyl)pyridazine

A mixture containing 40 g. of 3-amino-6-chloropyridazine and 240 ml. of morpholine was refluxed with stirring for 18 hours. The excess morpholine was distilled off in vacuo and the remaining material was dissolved in 250 ml. of warm water. To the aqueous solution was addes 29 ml. (0.34 mole) of concentrated sodium hydroxide solution; the resulting red solution was treated with about 1 g. of decolorizing charcoal and the water was distilled off in vacuo; about 1 liter of benzene was added to the residue and the benzene was then distilled off in vacuo. The residue was crystallized from 300 ml. of isopropyl alcohol and then recrystallized from 400 ml. of isopropyl alcohol and allowed to air-dry to produce 34.0 g. of 3-amino-6-(4-morpholinyl)-pyridazine, m.p. 131°–134° C.

D. CYCLIC ALKYLIDENYL N-[4(OR 5)-6-($R_3R_4N$)-3-PYRIDAZINYL]AMINOMETHYLENEMALONATES

D-1. Cyclic isopropylidenyl N-(6-dimethylamino-3-pyridazinyl)aminomethylenemalonate (also named 2,2-dimethyl-5-[(6-dimethylamino-3-pyridazinyl)aminomethylene]-1,3-dioxane-4,6-dione)

A stirred suspension containing 22 g. of 3-amino-6-dimethylaminopyridazine hydrochloride (Example C-1, first paragraph), 24.8 g. of triethyl orthoformate, 24.2 g. of cyclic isopropylidenyl malonate and 125 ml. of absolute ethanol was refluxed on a steam bath for 2 hours and the precipitated product was collected by filtering the hot reaction mixture. The precipitate was washed with a small quantity of ethanol and then was slurried up in 100 ml. of methanol and collected again. The washed product was then recrystallized from about 100 ml. of dimethylformamide, washed successively with dimethylformamide, ethanol and ether, and then dried in vacuo at 60° C. for about 15 hours to yield 9.9 g. of cyclic isopropylidenyl N-(6-dimethylamino-3-pyridazinyl)aminomethylenemalonate, m.p. 230° C. with decomposition.

A 25 g. portion of cyclic isopropylidenyl N-(6-dimethylamino-3-pyridazinyl)aminomethylenemalonate was dissolved in 25% aqueous sulfuric acid solution with very slight warming. The solution was poured into 1 liter of ethanol with stirring and the resulting mixture was cooled in an ice bath whereupon a precipitate separated. The precipitate was collected and dried to yield 18 g. of off-white solid. The same procedure was followed using another 25 g. portion of cyclic isopropylidenyl N-(6-dimethylamino-3-pyridazinyl)aminomethylenemalonate to yield another 18 g. of solid. The combined 36 g. of solid was recrystallized from methanol, washed with ether and dried to yield 24 g. of cyclic isopropylidenyl N-(6-dimethylamino-3-pyridazinyl)aminomethylenemalonate sulfate, m.p. >300° C.

In another preparation of cyclic isopropylidenyl N-(6-dimethylamino-3-pyridazinyl)aminomethylenemalonate, a slurry of 225 g. of 3-amino-6-dimethylaminopyridazine hydrochloride (Example C-1, second paragraph) in 2.3 liters of absolute ethanol was warmed to 55° C. and 360 g. of cyclic isopropylidenyl α-methoxymethylenemalonate was added all at once. The internal temperature rose to 60° C. and the reaction was then stirred for 30 minutes at 55° C. and then chilled. The resulting precipitate was collected, washed with cold ethanol and dried overnight in vacuo at 65° C. to yield 410 g. of the product. This 410 g. of product was combined with a 93 g. sample of product obtained from another run and the combination was recrystallized from four liters of dimethylformamide. A second crop was obtained by concentrating the filtrate from the dimethylformamide recrystallization to 400 ml. and chilling. Both crops were dried overnight in vacuo at 65° C. There was thus obtained, as the first crop, 404 g. of cyclic isopropylidenyl N-(6-dimethylamino-3-pyridazinyl)aminomethylenemalonate, m.p. 240°–242° C. and, as a second crop, 38 g. of said compound, m.p. 240°–242° C., the combined overall yield being 76%.

D-2. Cyclic isopropylidenyl N-(6-diethylamino-3-pyridazinyl)aminomethylenemalonate (also named 5-[(6-diethylamino-3-pyridazinyl)aminomethylene]-2,2-dimethyl-1,3-dioxane-4,6-dione)

A mixture containing 14 g. of 3-amino-6-diethylaminopyridazine (28 g. of Example C-2), 16 g. of cyclic isopropylidenyl α-methoxymethylenemalonate and 150 ml. of methanol was stirred at room temperature for four hours. A drop of the clear reaction mixture was placed on a watch glass and scratched with a glass rod whereupon crystallization resulted. The crystals were added to the reaction mixture which was then stirred for an additional hour at room temperature and then chilled in an ice bath. The resulting precipitate was collected, washed successively with methanol and ether, and dried. The crystalline product was recrystallized once from dimethylformamide and then once from ethanol, washed with ether and dried to yield 9 g. of cyclic isopropylidenyl N-(6-diethylamino-3-pyridazinyl)aminomethylemalonte, m.p. 169°–171° C.

D-3. Cyclic isopropylidenyl N-[6(4-morpholinyl)-3-pyridazinyl]aminomethylenemalonate (also named 2,2-dimethyl-5-{[6-(4-morpholinyl)-3-pyridazinyl]aminomethylene}-1,3-dioxane-4,6-dione)

A mixture containing 3.3 g. of 3-amino-6-(4-morpholinyl)pyridazine (11 g. of Example C-3), 11.2 g. of cyclic isopropylidenyl α-methylmethylenemalonate and 100 ml. of methanol was stirred at room temperature for 3 hours. The precipitated product was collected, washed successively with methanol and ether and dried; it was then recrystallized from dimethylformamide, washed successively with ethanol and ether, and dried to yield 2.5 g. of cyclic isopropylidenyl N-[6-(4-morpholinyl)-3-pyridazinyl]aminomethylenemalonate, m.p. 214°–216° C. with decomposition.

In another preparation of this compound, 33.5 g. of 3-amino-6-(4-morpholinyl)pyridazine (from Example C-42) was dissolved in 400 ml. of methanol at about 35°

C. and to the solution was added all at once with stirring a thin suspension containing 40.3 g. of cyclic isopropylidenyl α-methoxymethylenemalonate in 200 ml. of warm water whereupon a heavy precipitate formed immediately. The resulting thick suspension was stirred for thirty minutes and the precipitate was collected, recrystallized from 250 ml. of dimethylformamide at 100° C., washed with ether and dried in vacuo at 60° C. to yield 60 g. of cyclic isopropylidenyl N-[6-(4-morpholinyl)-3-pyridazinyl]aminomethylenemalonate, m.p. 219°–220° C. with decomposition.

D-4. Cyclic isopropylidenyl N-[6-(1-pyrrolidinyl)-3-pyridazinyl]aminomethylenemalonate (also named 2,2-dimethyl-5-{[6-(1-pyrrolidinyl)-3-pyridazinyl]aminomethylene}-1,3-dioxane-4,6-dione)

A mixture containing 8 g. of 3-amino-6-(1-pyrrolidinyl)pyridazine (16 g. of Example C-4 also containing an equal quantity of 3-chloro-6-(1-pyrrolidinyl)pyridazine), 9.3 g. of cyclic isopropylidenyl α-methoxymethylenemalonate and 100 ml. of methanol was stirred at room temperature for two hours and the precipitated product was collected, washed successively with isopropyl alcohol and ether, and dried. The product was then recrystallized from dimethylformamide, washed successively with ethanol and ether, and dried to yield 2.5 g. of cyclic isopropylidenyl N-[6-(1-pyrrolidinyl)-3-pyridazinyl]aminomethylenemalonate, m.p. 207°–209° C. with decomposition.

The following run was carried out using the intermediate 3-amino-6-(1-pyrrolidinyl)pyridazine prepared according to the procedure described in the second paragraph of Example C-4: to a stirred solution containing 53 g. of 3-amino-6-(1-pyrrolidinyl)pyridazine and 600 ml. of methanol at room temperature was added 62 g. of cyclic isopropylidenyl α-methoxymethylenemalonate in one portion whereupon the product formed almost at once. The reaction mixture was stirred at room temperature for 2½ hours and the crystalline product was collected, washed free of color using methanol and dried in a vacuum oven at 50° C. to yield 32 g. of cyclic isopropylidenyl N-[6-(1-pyrrolidinyl)-3-pyridazinyl]aminomethylenemalonate, m.p. 219°–220° C. with decomposition. More of the product can be isolated from the methanolic filtrate.

D-5. Cyclic isopropylidenyl N-[6-(1-piperidinyl)-3-pyridazinyl]aminomethylenemalonate (also named 2,2-dimethyl-5-{[6-(1-piperidinyl)-3-pyridazinyl]aminomethylene}-1,3-dioxane-4,6-dione)

To a solution containing 20.2 g. of a mixture (Example C-13) consisting mostly (up to 17.8 g.) of 3-amino-6-(1-piperidinyl)pyridazine and some piperidine hydrochloride dissolved in 300 ml. of dry methanol was added with stirring 18.6 g. of cyclic isopropylidenyl α-methoxymethylenemalonate whereupon dissolution resulted followed by separation of copious yellow solid. The solid was broken up and the mixture stirred for 75 minutes at room temperature and then allowed to stand overnight. The yellow solid was collected, washed with 40 ml. of fresh methanol and sucked dry to yield 5.7 g. of product, m.p. 206°–207° C. with decomposition. This product was combined with 4.7 g. of the same product obtained following the same procedure (using 12.0 g. of 3-amino-6-(1-piperidinyl)pyridazine, 150 ml. of absolute methanol and 9.3 g. of cyclic isopropylidenyl α-methoxymethylenemalonate) and the combined 10.4 g. of product was recrystallized from 350 ml. of absolute ethanol and dried in a vacuum oven at 80° C. to yield 9.4 g. of cyclic isopropylidenyl N-[6-(1-piperidinyl)-3-pyridazinyl]aminomethylenemalonate, m.p. 207°–208° C. with decomposition.

It is contemplated that following the procedure described in Example D-5 but using in place of 3-amino-6-(1-piperidinyl)pyridazine a molar equivalent quantity of the appropriate 3-amino-6-($R_3R_4N$)pyridazine, the cyclic isopropylidenyl N-[6-($R_3R_4N$)-3-pyridazinyl]aminomethylenemalonates of Examples D-6 and D-7 will be obtained:

D-6. Cyclic isopropylidenyl N-[6-(N-ethyl-N-methylamino)-3-pyridazinyl]aminomethylenemalonate using 3-amino-6-(N-ethyl-N-methylamino)pyridazine.

D-7. Cyclic isopropylidenyl N-(6-diisopropylamino-3-pyridazinyl)aminomethylenemalonate using 3-amino-6-diisopropylaminopyridazine.

D-8. Cyclic isopropylidenyl N-(6-di-n-propylamino-3-pyridazinyl)aminomethylenemalonate, 4 g., m.p. 179°–181° C., was obtained following the procedure of Example D-5 using 13 g. of 3-amino-6-di-n-propylaminopyridazine, 7.1 g. of cyclic isopropylidenyl α-methoxymethylenemalonate, 200 ml. of methanol and recrystallization from ethyl acetate.

D-9. Cyclic isopropylidenyl N-[6-(4-methyl-1-piperazinyl)-3-pyridazinyl]aminomethylenemalonate hydrochloride hemihydrate, 4.3 g., m.p. 229°–230° C. (dec.), was obtained following the procedure of Example D-5 using 33.7 g. of a mixture (Example C-14) containing 3-amino-6-(4-methyl-1-piperazinyl)pyridazine and a molar equivalent quantity of N-methylpiperazine hydrochloride, 18.6 g. of cyclic isopropylidenyl α-methoxymethylenemalonate, 300 ml. of methanol and recrystallization from dimethylformamide.

D-10. It is contemplated that cyclic 4-heptylidenyl N-(6-dimethylamino-3-pyridazinyl)aminomethylenemalonate will be produced by following the procedures described in Example D-1 (first and third paragraphs) but using in place of cyclic isopropylidenyl malonate (first paragraph) a molar equivalent quantity of cyclic isopropylidenyl α-methoxymethylenemalonate (third paragraph) a molar equivalent quantity of cyclic 4-heptylidenyl α-methoxymethylenemalonate.

Similarly, it is contemplated that following the procedures described in Examples D-1 (first and third paragraphs) but using in place of cyclic isopropylidenyl malonate (first paragraph) or cyclic isopropylidene α-methoxymethylenemalonate (third paragraph) a corresponding molar equivalent quantity of the appropriate respective cyclic alkylidenyl malonate or cyclic alkylidenyl α-methoxymethylenemalonate, the cyclic alkylidenyl N-(6-dimethylamino-3-pyridazinyl)aminomethylenemalonates of Example D-11 thru D-13 will be obtained:

D-11. Cyclic 3-pentylidenyl N-(6-dimethylamino-3-pyridazinyl)aminomethylenemalonate using cyclic 3-pentylidenyl malonate or cyclic 3-pentylidenyl α-methoxymethylenemalonate, respectively.

D-12. Cyclic 2-butylidenyl N-(6-dimethylamino-3-pyridazinyl)aminomethylenemalonate using cyclic 2-butylidenyl malonate or cyclic 2-butylidenyl α-methoxymethylenemalonate, respectively.

D-13. Cyclic 3-hexylidenyl N-(6-dimethylamino-3-pyridazinyl)aminomethylenemalonate using cyclic 3-hexylidenyl malonate or cyclic 3-hexylidenyl α-methoxymethylenemalonate, respectively.

It is contemplated that the intermediate cyclic alkylidenyl malonate derivatives of Example D-11, D-12 and D-13 will be prepared by the procedures given as follows for the preparation of cyclic 3-pentylidenyl malonate and cyclic 3-pentylidenyl α-methoxymethylenemalonate: A mixture containing 63.4 g. of malonic acid, 90 g. of 3-pentanone, 120 ml. of acetic anhydride and 2 ml. of concentrated sulfuric acid was stirred at 40° C. for about four hours and then allowed to stand at room temperature overnight. To the pale yellow solution was added about 200 ml. of cold water and about 300 ml. of ether. The mixture was shaken well and the aqueous layer was removed. The organic layer was extracted with 50 ml. portions of 2N aqueous potassium hydroxide solution until the extracts were basic. The combined extracts were washed twice with ether and then treated dropwise with concentrated hydrochloric acid until no additional oily material separated. The oily layer was extracted with ether, washed twice with water and once with saturated brine, dried over anhydrous magnesium sulfate and filtered. The filtrate was heated in vacuo to remove the ether, thereby yielding as a yellow oil 50 g. of cyclic 3-pentylidenyl malonate. A mixture containing 50 g. of cyclic 3-pentylidene malonate and 150 g. of trimethyl orthoformate was refluxed with stirring for three hours. The resulting clear solution was cooled in an ice-methanol bath. The crystalline precipitate was collected, washed with n-hexane and dried in vacuo to yield 25 g. of cyclic 3-pentylidenyl α-methoxymethylenemalonate, m.p. 85°–87° C. Following the procedures described for the preparation of cyclic 3-pentylidenyl malonate and cyclic 3-pentylidenyl α-methoxymethylenemalonate but using in place of 3-pentanone a molar equivalent quantity of 2-butanone or 3-hexanone, it is contemplated that there will be obtained, respectively, cyclic 2-butylidenyl malonate and cyclic 2-butylidenyl α-methoxymethylenemalonate or cyclic 3-hexylidenyl malonate and cyclic 3-hexylidenyl α-methoxymethylenemalonate.

D-14. Cyclic isopropylidenyl N-[6-(2,6-dimethyl-4-morpholinyl)-3-pyridazinyl]aminomethylenemalonate (also named 2,2-dimethyl-5-{[6-(2,6-dimethyl-4-morpholinyl)-3-pyridazinyl]aminomethylidine}-1,3-dioxane-4,6-dione)

A mixture containing 9 g. of 3-amino-6-(2,6-dimethyl-4-morpholinyl)pyridazine hydrochloride, 4.24 g. of cyclic isopropylidenyl α-methoxymethylenemalonate and 100 ml. of methanol was stirred at room temperature for two hours and then allowed to stand at room temperature overnight (15 hours). The solid precipitate was collected, dried and recrystallized from ethanol, washed with ether and dried to yield, as a white solid, 7 g. of cyclic isopropylidenyl N-[6-(2,6-dimethyl-4-morpholinyl)-3-pyridazinyl]aminomethylenemalonate hydrochloride, m.p. 212°–213° C. with decomposition.

In another run, a solution of 54 g. of 3-amino-6-(2,6-dimethyl-4-morpholinyl)pyridazine in 300 ml. of ethanol was filtered and the filtrate treated at once with a filtered solution of 52.0 g. of cyclic isopropylidenyl α-methoxymethylenemalonate in 250 ml. of 20% aqueous methanol. The reaction mixture was kept at 45° to 50° C. for thirty minutes and then chilled to 10° C. The precipitate was collected, washed successively with ethanol and ether, and dried in vacuo at 30° C. over the weekend to yield 92 g. of cyclic isopropylidenyl N-[6-(2,6-dimethyl-4-morpholinyl)-3-pyridazinyl]aminomethylenemalonate, m.p. 196°–198° C.

D-15. Cyclic isopropylidenyl N-(5-methyl-6-dimethylamino-3-pyridazinyl)aminomethylenemalonate (also named 2,2-dimethyl-5-[(5-methyl-6-dimethylamino-3-pyridazinyl)aminomethylidine]-1,3-dioxane-4,6-dione)

A stirred mixture containing 10.5 g. of 3-amino-5-methyl-6-dimethylaminopyridazine, 7.5 g. of cyclic isopropylidenyl α-methoxymethylenemalonate and 100 ml. of methanol was refluxed overnight (about fifteen hours) and then allowed to cool to room temperature. The solid was collected, recrystallized from dimethylformamide, washed successively with methanol and ether and dried to produce 10.5 g. of cyclic isopropylidenyl N-(5-methyl-6-dimethylamino-3-pyridazinyl)aminomethylenemalonate, m.p. 211°–213° C. with decomposition.

It is contemplated that following the procedure described in Example D-14, second paragraph, but using in place of 3-amino-6-(2,6-dimethyl-4-morpholinyl)-pyridazine a molar equivalent quantity of the appropriate 3-amino-6-(alkylated-4-morpholinyl)pyridazine, there will be obtained the following respective cyclic isopropylidenyl N-[6-(alkylated-4-morpholinyl)-3-pyridazinyl]aminomethylenemalonates of Examples D-16 thru D-35.

D-16. Cyclic isopropylidenyl N-[6-(2-methyl-4-morpholinyl)-3-pyridazinyl]aminomethylenemalonate using 3-amino-6-(2-methyl-4-morpholinyl)pyridazine.

D-17. Cyclic isopropylidenyl N-[6-(3-methyl-4-morpholinyl)-3-pyridazinyl]aminomethylenemalonate using 3-amino-6-(3-methyl-4-morpholinyl)pyridazine.

D-18. Cyclic isopropylidenyl N-[6-(2-ethyl-4-morpholinyl)-3-pyridazinyl]aminomethylenemalonate using 3-amino-6-(2-ethyl-4-morpholinyl)pyridazine.

D-19. Cyclic isopropylidenyl N-[6-(3-ethyl-4-morpholinyl)-3-pyridazinyl]aminomethylenemalonate using 3-amino-6-(3-ethyl-4-morpholinyl)pyridazine.

D-20. Cyclic isopropylidenyl N-[6-(2-n-propyl-4-morpholinyl)-3-pyridazinyl]aminomethylenemalonate using 3-amino-6-(2-n-propyl-4-morpholinyl)pyridazine.

D-21. Cyclic isopropylidenyl N-[6-(2-isopropyl-4-morpholinyl)-3-pyridazinyl]aminomethylenemalonate using 3-amino-6-(2-isopropyl-4-morpholinyl)pyridazine.

D-22. Cyclic isopropylidenyl N-[6-(3-n-propyl-4-morpholinyl)-3-pyridazinyl]aminomethylenemalonate using 3-amino-6-(3-n-propyl-4-morpholinyl)pyridazine.

D-23. Cyclic isopropylidenyl N-[6-(2,3-dimethyl-4-morpholinyl)-3-pyridazinyl]aminomethylenemalonate using 3-amino-6-(2,3-dimethyl-4-morpholinyl)pyridazine.

D-24. Cyclic isopropylidenyl N-[6-(2,5-dimethyl-4-morpholinyl)-3-pyridazinyl]aminomethylenemalonate using 3-amino-6-(2,5-dimethyl-4-morpholinyl)pyridazine.

D-25. Cyclic isopropylidenyl N-[6-(3,5-dimethyl-4-morpholinyl)-3-pyridazinyl]aminomethylenemalonate using 3-amino-6-(3,5-dimethyl-4-morpholinyl)pyridazine.

D-26. Cyclic isopropylidenyl N-[6-(3,3-dimethyl-4-morpholinyl)-3-pyridazinyl]aminomethylenemalonate using 3-amino-6-(3,3-dimethyl-4-morpholinyl)pyridazine.

D-27. Cyclic isopropylidenyl N-[6-(2-ethyl-5-methyl-4-morpholinyl)-3-pyridazinyl]aminomethylenemalonate using 3-amino-6-(2-ethyl-5-methyl-4-morpholinyl)pyridazine.

D-28. Cyclic isopropylidenyl N-[6-(5-ethyl-3-methyl-4-morpholinyl)-3-pyridazinyl]aminomethylenemalonate using 3-amino-6-(5-ethyl-3-methyl-4-morpholinyl)pyridazine.

D-29. Cyclic isopropylidenyl N-[6-(5-ethyl-2-methyl-4-morpholinyl)-3-pyridazinyl]aminomethylenemalonate using 3-amino-6-(5-ethyl-2-methyl-4-morpholinyl)pyridazine.

D-30. Cyclic isopropylidenyl N-[6-(2,6-diethyl-4-morpholinyl)-3-pyridazinyl]aminomethylenemalonate using 3-amino-6-(2,6-diethyl-4-morpholinyl)pyridazine.

D-31. Cyclic isopropylidenyl N-[6-(2,3,5-trimethyl-4-morpholinyl)-3-pyridazinyl]aminomethylenemalonate using 3-amino-6-(2,3,5-trimethyl-4-morpholinyl)pyridazine.

D-32. Cyclic isopropylidenyl N-[6-(2,3,3-trimethyl-4-morpholinyl)-3-pyridazinyl]aminomethylenemalonate using 3-amino-6-(2,3,3-trimethyl-4-morpholinyl)pyridazine.

D-33. Cyclic isopropylidenyl N-[6-(5-ethyl-2,3-dimethyl-4-morpholinyl)-3-pyridazinyl]aminomethylenemalonate using 3-amino-6-(5-ethyl-2,3-dimethyl-4-morpholinyl)pyridazine.

D-34. Cyclic isopropylidenyl N-[6-(2,2,6,6-tetramethyl-4-morpholinyl)-3-pyridazinyl]aminomethylenemalonate using 3-amino-6-(2,2,6,6-tetramethyl-4-morpholinyl)pyridazine.

D-35. Cyclic isopropylidenyl N-[6-(3,3,5,5-tetramethyl-4-morpholinyl)-3-pyridazinyl]aminomethylenemalonate using 3-amino-6-(3,3,5,5-tetramethyl-4-morpholinyl)pyridazine.

E. CYCLIC ISOPROPYLIDENYL N-(6-METHYLAMINO-3-PYRIDAZINYL)AMINOMETHYLENEMALONATE

E-1. 3-Amino-6-methylaminopyridazine

A mixture containing 39 g. of 3-amino-6-chloropyridazine, 80 ml. of 40% aqueous methylamine and 550 ml. of ethanol was autoclaved at 150° C. for twenty-four hours. The reaction mixture was distilled in vacuo to remove the solvent and the excess aqueous methylamine. The residue was dissolved in water, neutralized with 2N potassium hydroxide solution and the liquid distilled off in vacuo to remove the solvent and the excess aqueous methylamine. The residue was dissolved in water, neutralized with 2N potassium hydroxide solution and the liquid distilled off in vacuo. The residue was taken up in methanol, the solution treated with decolorizing charcoal and filtered, and the filtrate heated in vacuo to remove the methanol. The residue was dissolved in 6N hydrochloric acid and the liquid distilled off in vacuo. The remaining crystalline material was recrystallized from ethanol, washed with ether and dried to yield 40 g. of 3-amino-6-methylaminopyridazine hydrochloride as a tan solid. This product was used in the subsequent step (Example E-2) without any further purification.

E-2. Cyclic isopropylidenyl N-(6-methylamino-3-pyridazinyl)aminomethylenemalonate (also named 2,2-dimethyl-5-[(3-methylamino-6-pyridazinyl)aminomethylene]-1,3-dioxane-4,6-dione)

A mixture containing 35 g. of 3-amino-6-methylaminopyridazine hydrochloride, 47 g. of cyclic isopropylidenyl α-methoxymethylenemalonate, 500 ml. of methanol and 5 ml. of triethylamine was stirred at room temperature overnight and then chilled in an ice bath. The precipitated product was collected, washed with ether, dried, and recrystallized from methanol to yield 14 g. of cyclic isopropylidenyl N-(6-methylamino-3-pyridazinyl)aminomethylenemalonate hydrochloride, m.p. 228°–229° C. with decomposition.

The usefulness of the compounds of formulas I and II as schistosomicidal agents is demonstrated by their effectiveness in proven chemotherapeutic in vivo test procedures in animals, e.g., mice and hamsters, against at least two of the three species which cause the disease in higher animals, including man, viz., *Schistosoma mansoni*, *Schistosoma japonicum* and *Schistosoma haematobium*. For example, when administered orally to 18–22 g. female Swiss-Webster mice or to 70–80 g. male or female Syrian hamsters infected with *S. mansoni* or to said mice infected with *S. japonicum* or to said hamsters infected with *S. haematobium*, preferred embodiments of these compounds (I and II) were found to clear completely the animals of all of the said parasitic infections at varying dose levels, e.g., their $ED_{50}$ values ranging from about 15 to 200 mg./kg. per day for five days when administered orally, with $ED_{50}$ values of other embodiments ranging from about 100 to 400 mg./kg. per day orally for five days. These proven chemotherapeutic in vivo procedures for in vivo screening and evaluation of schistosomicides are described by Yarinsky [J. of Toxicology and Environmental Health 1, 229–242 (1975)].

The actual determination of the numerical schistosomicidal data definitive for a particular compound of the invention is readily obtained according to the above-designated in vivo schistosomicidal test procedures by technicians versed in schistosomicidal test procedures, without any need for any extensive experimentation.

The present invention includes within its scope a schistosomicidal composition which comprises as the active ingredient a schistosomicidally effective cyclic alkylidenyl N-[6-($R_3R_4N$)-3-pyridazinyl]aminomethylenemalonate having formula I or cyclic isopropylidenyl N-(6-methylamino-3-pyridazinyl)aminomethylenemalonate or pharmaceutically-acceptable acid-addition salt thereof in admixture with a pharmaceutically acceptable carrier. The invention also includes within its scope a method for the treatment of schistosomiasis which comprises administering orally to a host infected with schistosomes a schistosomicidally effective amount of a compound selected from the group consisting of the cyclic alkylidenyl N-[6-($R_3R_4N$)-4(or 5)-$R_5$-3-pyridazinyl]aminomethylenemalonate having formula I, cyclic isopropylidenyl N-(6-methylamino-3-pyridazinyl)aminomethylenemalonate having formula II or pharmaceutically acceptable acid-addition salt thereof. In clinical practice the said compounds of formula I or II will normally be administered orally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate talc and the like.

Liquid compositions for oral administration include pharmaceutically acceptable emulsions, solutions, suspensions, syrups and elixirs containing inert diluents commonly used in the art, such as water, dimethyl sulfoxide and liquid paraffin. Besides inert diluents such compositions may also contain adjuvants, such as wetting and suspending agents, and sweetening, flavouring, perfuming and preserving agents. According to the invention, the compounds for oral administration also include as a pharmaceutically acceptable carrier capsules of absorbable material, such as gelatin, containing said active component with or without the addition of diluents or excipients.

The percentage of active component in the said composition and method for the treatment of schistosomiasis may be varied so that a suitable dosage is obtained. The dosage administered to a particular patient is variable, depending upon the clinician's judgement using as the criteria: the duration of treatment, the size and condition of the patient, the potency of the active component and the patient's response thereto. An effective dosage amount of active component can thus only be determined by the clinician considering all criteria and utilizing his best judgement on the patient's behalf.

We claim:
1. Cyclic alkylidenyl N-[6-($R_3R_4N$)-4(or 5)-$R_5$-3-pyridazinyl]aminomethylenemalonate having the formula

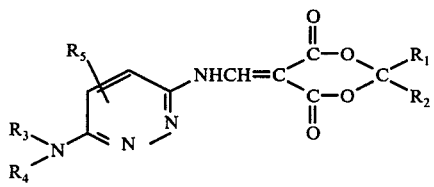

wherein
$R_1$ and $R_2$ are each lower-alkyl having from one to three carbon atoms;
$R_3$ and $R_4$ are each lower-alkyl having from one to three carbon atoms or $R_3R_4N$ is 1-piperidinyl, 1-pyrrolidinyl, 4-methyl-1-piperazinyl, 4-morpholinyl or 4-morpholinyl having from one to four ring-carbon alkyl substituents selected from methyl, ethyl, n-propyl and isopropyl with the total number of carbon atoms of the alkyl substituent or substituents being from one to four;
$R_5$ is hydrogen or lower-alkyl having from one to three carbon atoms; or
pharmaceutically acceptable salt thereof.

2. A compound according to claim 1 where $R_1$ and $R_2$ are each methyl.

3. Cyclic isopropylidenyl N-(6-dimethylamino-3-pyridazinyl)aminomethylenemalonate or pharmaceutically acceptable salt thereof.

4. Cyclic isopropylidenyl N-(6-diethylamino-3-pyridazinyl)aminomethylenemalonate according to claim 2 where $R_3R_4N$ is diethylamino.

5. Cyclic isopropylidenyl N-[6-(4-morpholinyl)-3-pyridazinyl]aminomethylenemalonate according to claim 2 where $R_3R_4N$ is 4-morpholinyl.

6. Cyclic isopropylidenyl N-[6-(1-pyrrolidinyl)-3-pyridazinyl]aminomethylenemalonate according to claim 2 where $R_3R_4N$ is 1-pyrrolidinyl.

7. Cyclic isopropylidenyl N-[6-(2,6-dimethyl-4-morpholinyl)-3-pyridazinyl]aminomethylenemalonate or pharmaceutically acceptable salt thereof.

8. Cyclic isopropylidenyl N-(6-methylamino-3-pyridazinyl)aminomethylenemalonate.

9. A schistosomicidal composition which comprises as the active component a schistosomicidally effective cyclic alkylidenyl N-[6-($R_3R_4N$)-4(or 5)-$R_5$-3-pyridazinyl]aminomethylenemalonate having the formula

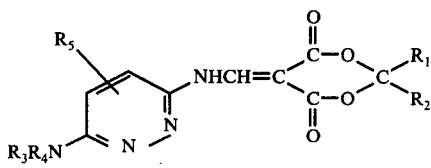

or cyclic isopropylidenyl N-(6-methylamino-3-pyridazinyl)aminomethylenemalonate or pharmaceutically acceptable acid-addition salt thereof in admixture with a pharmaceutically acceptable carrier, wherein
$R_1$ and $R_2$ are each lower-alkyl having from one to three carbon atoms;
$R_3$ and $R_4$ are each lower-alkyl having from one to three carbon atoms or $R_3R_4N$ is 1-piperidinyl, 1-pyrrolidinyl, 4-methyl-1-piperazinyl, 4-morpholinyl or 4-morpholinyl having from one to four ring-carbon alkyl substituents selected from methyl, ethyl, n-propyl and isopropyl with the total number of carbon atoms of the alkyl substituent or substituents being from one to four; and,
$R_5$ is hydrogen or lower-alkyl having from one to three carbon atoms.

10. A composition according to claim 9 where the active component is said compound where $R_1$ and $R_2$ are each methyl.

11. A composition according to claim 10 where the active component is cyclic isopropylidenyl N-(6-dimethylamino-3-pyridazinyl)aminomethylenemalonate.

12. A composition according to claim 10 where the active component is cyclic isopropylidenyl N-[6-(2,6-dimethyl-4-morpholinyl)-3-pyridazinyl]aminomethylenemalonate.

13. A method for the treatment of schistosomiasis which comprises administering orally to a host infected with schistosomes a schistosomicidally effective amount of a compound selected from the group consisting of cyclic alkylidenyl N-[6-($R_3R_4N$)-4(or 5)-$R_5$-3-pyridazinyl]aminomethylenemalonate of claim 1, cyclic isopropylidenyl N-(6-methylamino-3-pyridazinyl)aminomethylenemalonate or pharmaceutically acceptable acid-addition salt thereof, where $R_3R_4N$, $R_1$, $R_2$ and $R_5$ are each defined as in claim 1.

14. The method according to claim 13 where $R_1$ and $R_2$ are each methyl.

15. The method according to claim 14 where the schistosomicidally effective compound is cyclic isopropylidenyl N-(6-dimethylamino-3-pyridazinyl)aminomethylenemalonate or pharmaceutically acceptable acid-addition salt thereof.

16. The method according to claim 14 where the schistosomicidally effective compound is cyclic isopropylidenyl N-[6-(2,6-dimethyl-4-morpholinyl]aminomethylenemalonate or pharmaceutically acceptable acid-addition salt thereof.

17. A composition according to claim 10 where the active component is cyclic isopropylidenyl N-(6-methylamino-3-pyridazinyl)aminomethylenemalonate or pharmaceutically acceptable acid-addition salt thereof.

18. A method according to claim 14 where the schistosomicidally effective compound is cyclic isopropylidenyl N-(6-methylamino-3-pyridazinyl)aminomethylenemalonate or pharmaceutically acceptable acid-addition salt thereof.

* * * * *

UNITED STATES PATENT AND TRADEMARK OFFICE
CERTIFICATE OF CORRECTION

PATENT NO. : 4,104,385
DATED : August 1, 1978
INVENTOR(S) : George Y. Lesher and Chester J. Opalka, Jr.

It is certified that error appears in the above-identified patent and that said Letters Patent are hereby corrected as shown below:

Column 9, line 66, "3-amino-6-amino-6-(1-pyrrolidinyl)pyridazine" should read -- 3-amino-6-(1-pyrrolidinyl)-pyridazine --.

Column 14, line 56, "α-methylmethylenemalonate" should read -- α-methoxymethylenemalonate --.

Signed and Sealed this

Fifth Day of August 1980

[SEAL]

Attest:

SIDNEY A. DIAMOND

Attesting Officer

Commissioner of Patents and Trademarks